United States Patent [19]

Wuthrich et al.

[11] 4,059,110
[45] Nov. 22, 1977

[54] CLOCKWORK DRIVEN HYPODERMIC SYRINGE

[75] Inventors: Paul Wuthrich, Watertown; Paul Flumm, Oakville, both of Conn.

[73] Assignee: Timex Corporation, Waterbury, Conn.

[21] Appl. No.: 730,557

[22] Filed: Oct. 7, 1976

[51] Int. Cl.² ............................................. A61M 5/20
[52] U.S. Cl. ........................... 128/218 A; 128/DIG. 1
[58] Field of Search .......... 128/218 A, 218 R, 218 F, 128/234, 236, DIG. 1, 214 R, 214 F, 215

[56] References Cited

U.S. PATENT DOCUMENTS

| | | | |
|---|---|---|---|
| 2,602,446 | 7/1952 | Glass et al. | 128/218 A |
| 3,297,210 | 1/1967 | Lucas | 128/DIG. 1 |
| 3,415,419 | 12/1968 | Jewett et al. | 128/218 A X |
| 3,858,581 | 1/1975 | Kamen | 128/218 A |
| 3,886,938 | 6/1975 | Szabo et al. | 128/218 A |
| 4,006,736 | 2/1977 | Kranys et al. | 128/218 A X |

FOREIGN PATENT DOCUMENTS 2,276,841   1/1976   France ............................. 128/218 A

*Primary Examiner*—John D. Yasko
*Attorney, Agent, or Firm*—William C. Crutcher

[57] ABSTRACT

A clockwork device for driving a hypodermic syringe comprises a device for holding a syringe and automatically injecting predetermined amounts of fluid into a patient at a controlled rate over a period of time. The device comprises a clockwork mechanism, a syringe coupled thereto and an exterior housing containing the various components. The clockwork mechanism is mounted parallel to the overall length of the syringe within the housing to minimize the size of the device. A two-way releasable clutch is utilized to connect the clockwork mechanism to the syringe driving mechanism for ease of retracting or advancing the driving mechanism.

6 Claims, 6 Drawing Figures

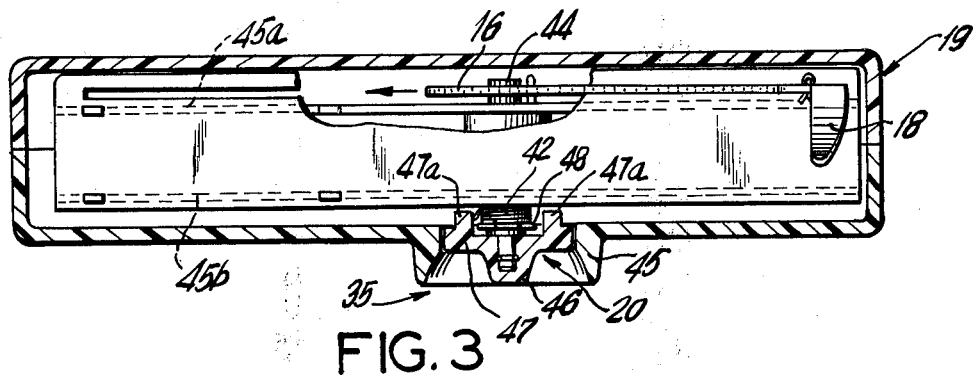
FIG. 3
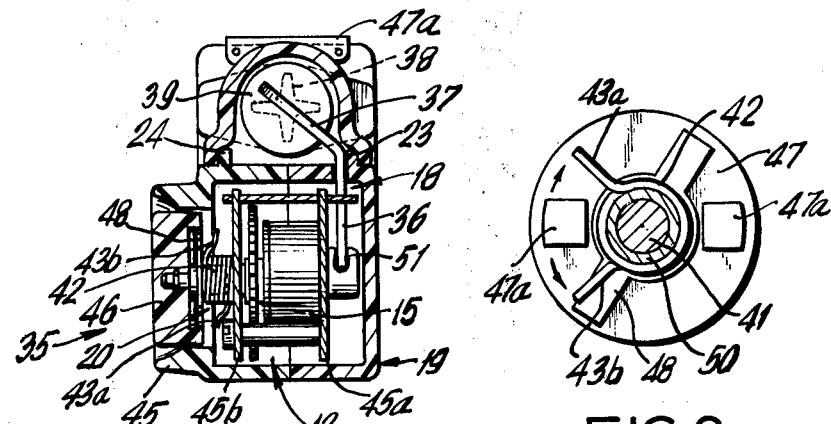
FIG. 4
FIG. 6
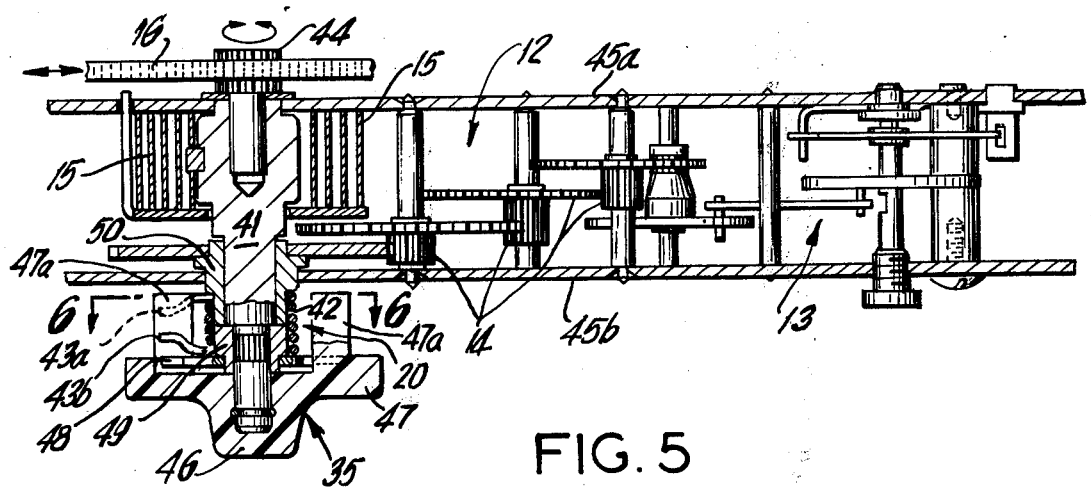
FIG. 5

CLOCKWORK DRIVEN HYPODERMIC SYRINGE

BACKGROUND OF THE INVENTION

This invention relates to a fluid infusion device such as hypodermic syringes and particularly to automatic mechanically-powered infusion devices.

The prior art discloses various mechanically-powered hypodermic syringes for medical or laboratory purposes. U.S. Pat. No. 3,886,938 to Sabo and Del Geurcio, which issued June 3, 1975 discloses a device which applies a driving force to a syringe under the control of conventional spring driven clockwork gear trains through a rack and pinion mechanism and is typical of the prior art in this area. In contrast to the present invention wherein a clockwork mechanism is mounted parallel to the overall length of the syringe, the clockwork mechanism of Sabo et al employs a rack and pinion gear in tandem with the syringe thereby increasing the overall length of the unit. In portable infusion devices, the increased length is a definite disadvantage and even in stationary devices, the overall unit size is a definite design consideration.

U.S. Pat. No. 2,764,980 to W. R. Smith which issued Oct. 2, 1956 discloses a continuous injection machine employing a reciprocating rack coupled to a hypodermic syringe. This disclosure is particularly suited for operating multiple syringes in a laboratory environment. Another prior art disclosure, U.S. Pat. No. 3,279,653 to F. W. Pfleger, which issued Oct. 18, 1966, discloses an escapement-controlled dispensing apparatus of a rather complicated type including drums and pulleys.

Prior art U.S. Pat. No. 3,685,967 to Caslow et al discloses a portable infusion pump for injecting fluids from a collapsible receptacle over an extended period of time. This patent does not employ a typical escapement mechanism but the pump is, nevertheless, controlled by a force constant spring which in turn is regulated by a timing device.

Further prior art of interest includes U.S. Pat. No. 2,498,652 to G. B. Glass which issued Feb. 28, 1950, U.S. Pat. No. 3,605,765 to P. Koltzman which issued Aug. 5, 1952 and British Patent 1,026,593 which was published Apr. 20, 1966. None of these prior art patents appear pertinent to the clockwork driven syringe of the present invention which contains unique features facilitating the widespread adoption of the device. Notably, the present invention is relatively small and portable due to the internal construction thereof, comparatively simple to manufacture, and inexpensive.

Accordingly, an object of this invention is to provide a new and improved mechanically powered syringe for the infusion of fluids into individuals.

Another object of this invention is to provide a new and improved portable clockwork driven syringe which is small in size and efficient in operation.

A more specific object of this invention is to provide a new and improved clockwork driven syringe which includes a unique two-way clutch which aids the mounting of the clockwork mechanism parallel to the syringe thereby lessening the overall size of the device.

SUMMARY OF THE INVENTION

The present invention relates to a device comprising a syringe driving mechanism, a housing adapted for holding a syringe mounted therein, a clockwork mechanism for controllably restraining the driving mechanism, and means coupling the clockwork mechanism to the syringe driving mechanism to permit driving the syringe at a predetermined rate. The clockwork mechanism is mounted adjacent to the extended syringe to minimize the length of the device. A two-way releasing clutch is provided, comprising a wire-wound coil spring having legs extending at each end which are separately engageable by a web on a loosely fitting setting knob. The spring can be loosened from its grip fit at either end by opposite rotational movement thus providing a two-way releasing function. Thus, the use of a wire-wound clutch spring permits a very high degree of strength to be applied for restraining the mainspring torque with the clockwork mechanism while requiring only a small proportion of this strength to be applied to either end of the spring for slipping the clutch spring in either desired direction.

BRIEF DESCRIPTION OF THE DRAWINGS

Other objects and advantages of this invention may be seen from the following description when viewed in conjunction with the accompanying drawings wherein:

FIG. 3 is a view of the subject invention taken along lines 3—3 of FIG. 2, FIG. 4 is a view of the invention taken along lines 4—4 of FIG. 2, and, FIG. 5 is a view of the invention taken along lines 5—5 of FIG. 2, FIG. 6 is a cross-section view along lines 6—6 of FIG. 5.

DETAILED DESCRIPTION OF THE INVENTION

Figure 1:
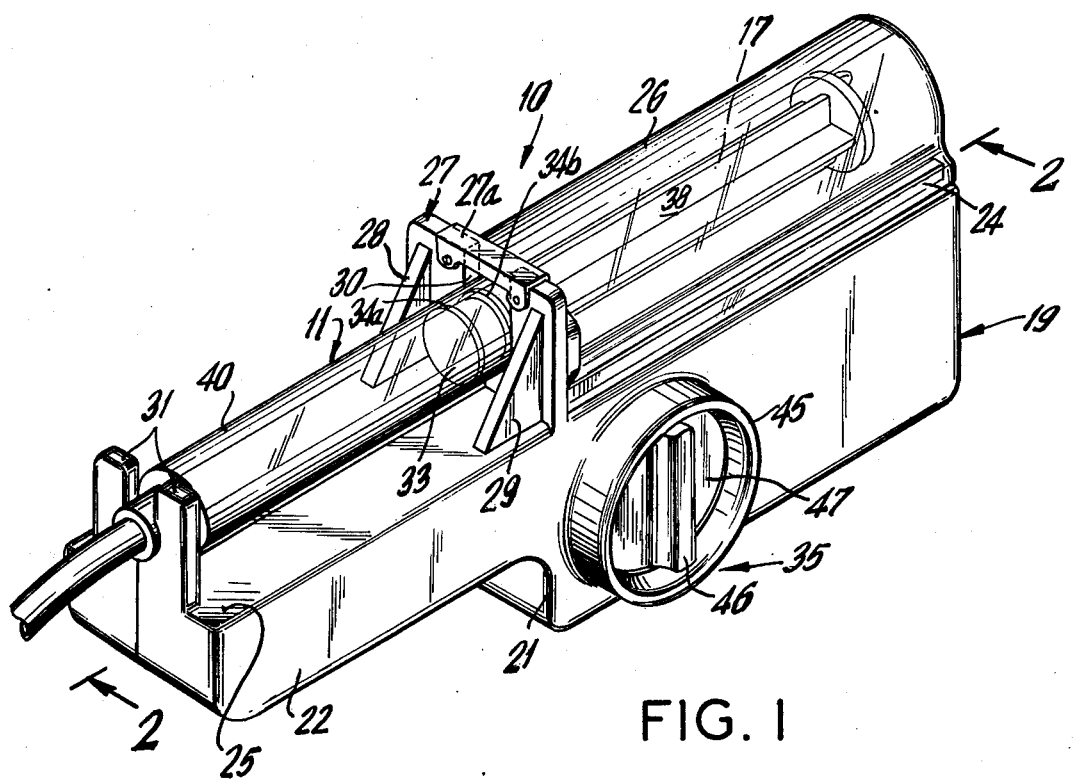
FIG. 1 is a perspective view of the clockwork driven syringe comprising the present invention.

Referring now to the drawings, the invention comprises a mechanically driven hypodermic device 10 which includes means for holding a hypodermic syringe 11 and a clockwork mechanism 12 which drives the syringe 11 at a controlled rate to administer a predetermined amount of a drug to a patient over an extended period of time.

The hypodermic syringe 11 may be a separate and standard conventional unit of a type known to the medical profession and fitted with a flexible tube and needle (not shown). The clockwork mechanism 12 is mounted in a shaped housing 19 and includes a typical escapement 13 and associated gear train 14 powered by a mainspring 15. The mainspring 15 drives a rack 16 having an arm 18 which engages the hypodermic plunger 17. A two-way releasing clutch 20 is provided to hold the power of the mainspring 15 with a high degree of strength while readily permitting movement in the desired direction.

The clockwork mechanism 12 is mounted in the plastic housing 19 which comprises an enlarged portion 21 adjacent to the extended plunger 17 and a relatively smaller forward portion 22 parallel to the syringe 11. The housing 19 includes a pair of spaced guide tracks 23 and 24 on its upper surface 25 which engage a clear plastic cover 26 which fits over the plunger 17. A bifurcated transverse member 27 having supporting struts 28 and 29 and a centrally located aperture 30 extends upwardly from the housing surface 25 at an intermediate location to support one end of syringe 11, while a bifurcated end portion 31 extends upwardly from the forward portion 22 of the housing 19 to support the other end of syringe 11. An engaging latch 27a is provided on the member 27 to lock the syringe 11 in place.

The syringe 11 comprises an elongated tube 40 having a plunger 17 which is slidable therein to force fluid out through the orifice 32. The plunger 17 includes a forward portion 33 having a pair of circumferential protrusions 34a and 34b connected to a cross-shaped stem 38. The protrusions effect a water tight seal so that the fluid is properly forced out without leakage during the forward movement of the stem 38. The syringe 11 is locked in the bifurcated supporting means 27 and 31 so that it may be readily replaced when a further infusion is required. The cover 26 is indented at a position adjacent to the member 27. Release of the engaging latch 27a permits the cover to be slid back on guides 23, 24 so that the syringe assembly 11 comprising the tube 40 and plunger 17 may be readily set therein.

Figure 2:
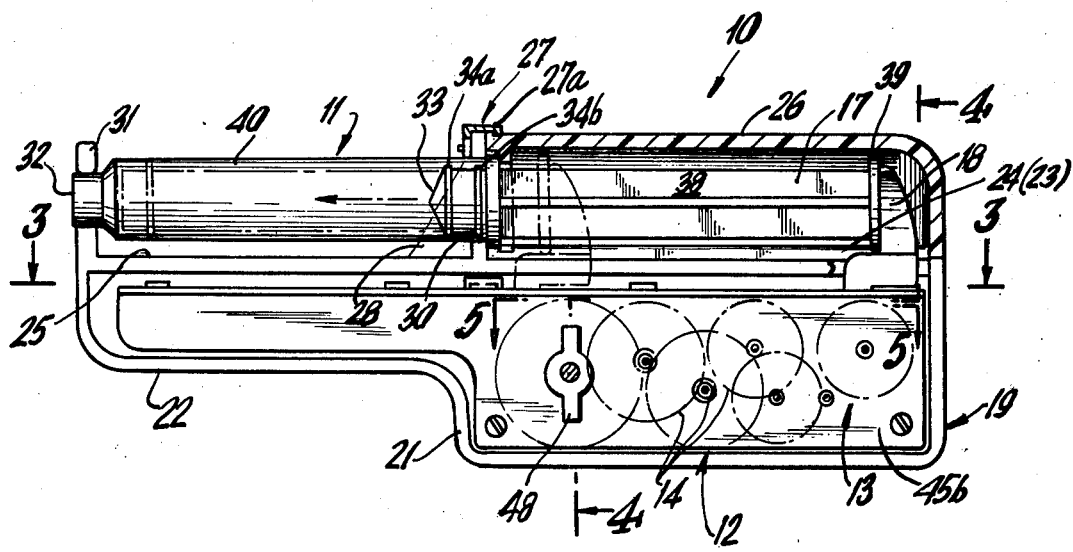
FIG. 2 is a view of the invention taken along the lines 2—2 of FIG. 1.

The driving arm 18 comprises a lower flat elongated portion 36 which has teeth on its edge comprising the rack 16 and an angular upper portion 37 which engages the protruding rear portion 39 of the plunger 17. The plunger driving arm 18 will normally be in its lowered position, as shown in phantom in FIG. 2, after an infusion operation. It may then be readily moved to its raised position, see FIG. 2, by clockwise rotation of the recessed setting knob 35 which releases the clutch 20 in a manner to be described. This will permit removal of the spent syringe 11 and insertion of a filled syringe 11 in its place. The clear (transparent) plastic cover 26 is closed and locked in place by the latching arrangement.

The recessed knob 35 is turned counter-clockwise to again release the clutch 20 and lower the driving arm 18 into engagement with the plunger 17 and to expel any air from the syringe 11 and needle (not shown). The entire unit 10 is now ready for attachment to a patient by means of a strap or other means which may or may not be integral to the unit 10. The hypodermic device 10 is then set to automatically inject a predetermined amount of fluid into a patient over a selected period of time.

A feature of the invention is the fact that the timing mechanism 12 is mounted parallel to the overall length of the syringe 11 (when the plunger 17 is in the extended position) in order to keep the overall length of the entire assembly to the minimal practical limits. In contrast to the other prior art of the type using a rack and pinion mechanism, the present invention additionally employs a two-way releasing clutch 20 to couple the clockwork mechanism 12 to the syringe driving mechanism. The clutch comprises a wire wound coil spring 42 mounted about a collar 49 attached to the winding shaft 41 and an adjacent collar 50. Collar 50 is connected to the final gear of the clockwork mechanism 12 and is a member rotatable with respect to the winding shaft 41. Each end of the spring 42 is extended to provide legs 43a and 43b which can be individually engaged by an integral inner web 47a in the loose fitting setting knob 35. FIG. 6 illustrates how the web 47a releases the spring clutch in either direction. Thus, it can be seen that the spring 42 can be loosened from its grip fit at either end by opposite rotational engagement thereby providing a two-way releasing function of the one-way clutch.

As a further advantage of the present design, the wire wound clutch spring 42 provides a high degree of strength for coupling the clockwork mechanism to the syringe driving mechanism and restraining the mainspring torque, while only requiring a small proportion of this strength to be applied at either end of the spring for slipping the clutch spring in the desired direction. A ratchet device such as used in the prior art would be undesirable for holding the power of the mainspring since this would prohibit the manual lowering the driving arm as previously described. Furthermore, the strength of the conventional friction clutch is usually some multiple of the spring strength to be retained, and for this application the friction clutch strength added to the winding torque would make the device difficult to wind.

In the present arrangement, the setting knob 35 is recessed and enclosed within a cylindrical guard wall 45 formed in the housing and has a manually operated element 46 and a connected disc 47. The recessed setting knob 35 is thus designed to prevent accidental interference by clothing or bedding. A separate removable key might also be used to prevent accidental change in the time setting.

The clockwork mechanism 12 includes a typical clockwork gear train 14 and an escapement 13 of conventional design and hence, a detailed explanation thereof is not necessary.

The details of this arrangement 12 are quite clearly shown in FIG. 5 and the functioning thereof is well known. The syringe driving mechanism includes a gear pinion 44 attached to the winding shaft 41, which is attached to the mainspring 15. The pinion engages the teeth of the sliding gear rack 16 which is integral with the driving arm 18. Sliding rack 16 is thus positioned and retained by the slotted guides such as 51 attached to the framework walls 45a and 45b of the movement 12.

While the invention has been explained by a detailed description of a certain preferred embodiment, it is understood that various modifications and substitutions can be made to the invention without departing from the scope of the appended claims.

What is claimed is:

1. A clockwork device adapted for driving a syringe, wherein said syringe includes an elongated container for fluid and a plunger extending outwardly from the container and slideable therein, said clockwork device comprising:
   a housing,
   a clockwork mechanism having an escapement controlled gear train mounted within the housing adjacent to the plunger in an extended condition,
   a syringe driving mechanism adapted to be coupled to said clockwork mechanism and including a winding shaft with a mainspring mounted thereto and a pinion thereon engaging a rack adapted to drive the syringe plunger, and
   means coupling the clockwork mechanism to the syringe driving mechanism to drive the plunger at a predetermined rate controlled by the clockwork mechanism comprising a spring clutch mounted about the winding shaft to permit free rotation in one direction while restraining mainspring torque in the opposite direction.

2. A clockwork device in accordance with claim 1 wherein:
   the winding shaft includes a knob rotatable thereon and extending outwardly from the housing, and,
   the clutch comprises a coiled wire spring mounted about the winding shaft and having end portions protruding outwardly therefrom, said end portions being actuated by the knob to release the clutch in either rotational direction.

3. A clockwork device in accordance with claim 1 further including:

support means on said housing for mounting the syringe, said means including a bifurcated support at one end of the housing and an intermediate support having an aperture for holding the syringe, latching means on the intermediate support and guide means on the respective sides of the housing extending from the intermediate support to the other end thereof, and, a transparent cover engaging the guide means and locked in place by the latching means.

4. A clockwork device in accordance with claim 1 wherein:

the winding shaft includes a knob rotatable thereon and actuating the spring clutch, said knob comprising a protruding element extending outwardly from the housing for manual operation, and said housing having a cylindrical wall surrounding said protruding element for safety purposes.

5. A clockwork device in accordance with claim 1 wherein:

said rack has an arm mounted to one end thereof, comprising a lower portion extending upwardly through the housing and an upper portion extending at an angle to the lower portion to engage the rear of the plunger.

6. A clockwork device in accordance with claim 1 further including:

a clear plastic cover removably mounted on the housing over the extended plunger and wherein the housing comprises an enlarged rear portion having the clockwork mechanism mounted therein, and a smaller forward portion extending outwardly therefrom and having support means for the syringe container projecting upwardly at the end thereof.

* * * * *